United States Patent
Tzeng et al.

(10) Patent No.: US 11,633,862 B2
(45) Date of Patent: Apr. 25, 2023

(54) AUTOMATIC CONTROL METHOD OF MECHANICAL ARM AND AUTOMATIC CONTROL SYSTEM

(71) Applicant: Metal Industries Research & Development Centre, Kaohsiung (TW)

(72) Inventors: Jian-Jia Tzeng, Kaohsiung (TW); Sheng-Hong Yang, Kaohsiung (TW); Bo-Wei Pan, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 211 days.

(21) Appl. No.: 17/103,960

(22) Filed: Nov. 25, 2020

(65) Prior Publication Data
US 2022/0161438 A1    May 26, 2022

(51) Int. Cl.
*B25J 9/16* (2006.01)
*A61B 34/00* (2016.01)

(52) U.S. Cl.
CPC ............ *B25J 9/1697* (2013.01); *A61B 34/70* (2016.02); *B25J 9/161* (2013.01); *B25J 9/1679* (2013.01)

(58) Field of Classification Search
CPC ............ A61B 34/20; A61B 2034/2065; A61B 2034/2055; A61B 34/37; A61B 34/30; A61B 34/70; B25J 9/1679; B25J 9/161; B25J 9/1697; G06T 2207/10028; G06T 2207/10024
See application file for complete search history.

(56) References Cited

U.S. PATENT DOCUMENTS

| | | | |
|---|---|---|---|
| 2018/0260628 A1* | 9/2018 | Namiki | G06V 20/10 |
| 2019/0143517 A1 | 5/2019 | Yang et al. | |
| 2019/0261565 A1 | 8/2019 | Robertson et al. | |
| 2020/0061811 A1 | 2/2020 | Iqbal et al. | |
| 2020/0094405 A1 | 3/2020 | Davidson et al. | |
| 2020/0101613 A1 | 4/2020 | Yamada et al. | |
| 2020/0147804 A1* | 5/2020 | Sugiyama | G06T 7/73 |

FOREIGN PATENT DOCUMENTS

| | | |
|---|---|---|
| CN | 110825245 | 2/2020 |
| TW | 202034215 | 9/2020 |

OTHER PUBLICATIONS

"Office Action of Taiwan Counterpart Application", dated Jun. 18, 2021, p. 1-p. 9.

* cited by examiner

*Primary Examiner* — Jonathan L Sample
*Assistant Examiner* — Elizabeth Rose Neleski
(74) *Attorney, Agent, or Firm* — JCIPRNET

(57) ABSTRACT

An automatic control method of a mechanical arm and an automatic control system are provided. The automatic control method includes the following steps: obtaining a color image and depth information corresponding to the color image through a depth camera; performing image space cutting processing and image rotation processing according to the color image and the depth information to generate a plurality of depth images; inputting the depth images into an environmental image recognition module such that the environmental image recognition module outputs a displacement coordinate parameter; and outputting the displacement coordinate parameter to a mechanical arm control module such that the mechanical arm control module controls the mechanical arm to move according to the displacement coordinate parameter.

16 Claims, 5 Drawing Sheets

AUTOMATIC CONTROL METHOD OF MECHANICAL ARM AND AUTOMATIC CONTROL SYSTEM

BACKGROUND

Technical Field

The disclosure relates to a control method and a system, and in particular, to an automatic control method of a mechanical arm and an automatic control system.

Description of Related Art

With the evolution of medical equipment, development of related medical equipment that may be automatically controlled to facilitate efficiency of medical personnel and accuracy of surgery is an important issue in this field. In particular, during the operation, the mechanical arm used to assist or work with the medical personnel (operator) to perform related operations is important. Nevertheless, in the existing mechanical arm design, in order for the mechanical arm to achieve the function of automatic control, the mechanical arm is required to be provided with a plurality of sensors, and a user has to perform tedious manual correction operations during each operation, so the mechanical arm may avoid obstacles in the path when moving and achieve results of accurate automatic movement and automatic operation. In view of the above, a new type of automatic control system design is provided as follows.

SUMMARY

The disclosure provides an automatic control method of a mechanical arm and an automatic control system through which the mechanical arm may be operated to move in a space and to effectively avoid an obstacle.

An automatic control method of a mechanical arm provided by the disclosure includes the following steps. A color image and depth information corresponding to the color image are obtained through a depth camera. Image space cutting processing and image rotation processing are performed according to the color image and the depth information to generate a plurality of depth images. The depth images are inputted into an environmental image recognition module such that the environmental image recognition module outputs a displacement coordinate parameter. The displacement coordinate parameter is outputted to a mechanical arm control module such that the mechanical arm control module controls the mechanical arm to move according to the displacement coordinate parameter.

An automatic control system of a mechanical arm provided by the disclosure includes a depth camera and a processor. The depth camera is configured to obtain a color image and depth information corresponding to the color image. The processor is coupled to the mechanical arm and the depth camera. The processor is configured to perform image space cutting processing and image rotation processing according to the color image and the depth information to generate a plurality of depth images. The processor inputs the depth images into an environmental image recognition module such that the environmental image recognition module outputs a displacement coordinate parameter. The processor outputs the displacement coordinate parameter to a mechanical arm control module such that the mechanical arm control module controls the mechanical arm to move according to the displacement coordinate parameter.

To sum up, in the automatic control method of the mechanical arm and the automatic control system provided by the disclosure, the obstacle in the current environment may be automatically determined through visual training, and the mechanical arm may be effectively operated to move in the current environment.

To make the aforementioned more comprehensible, several embodiments accompanied with drawings are described in detail as follows.

DESCRIPTION OF THE EMBODIMENTS

Figure 1:
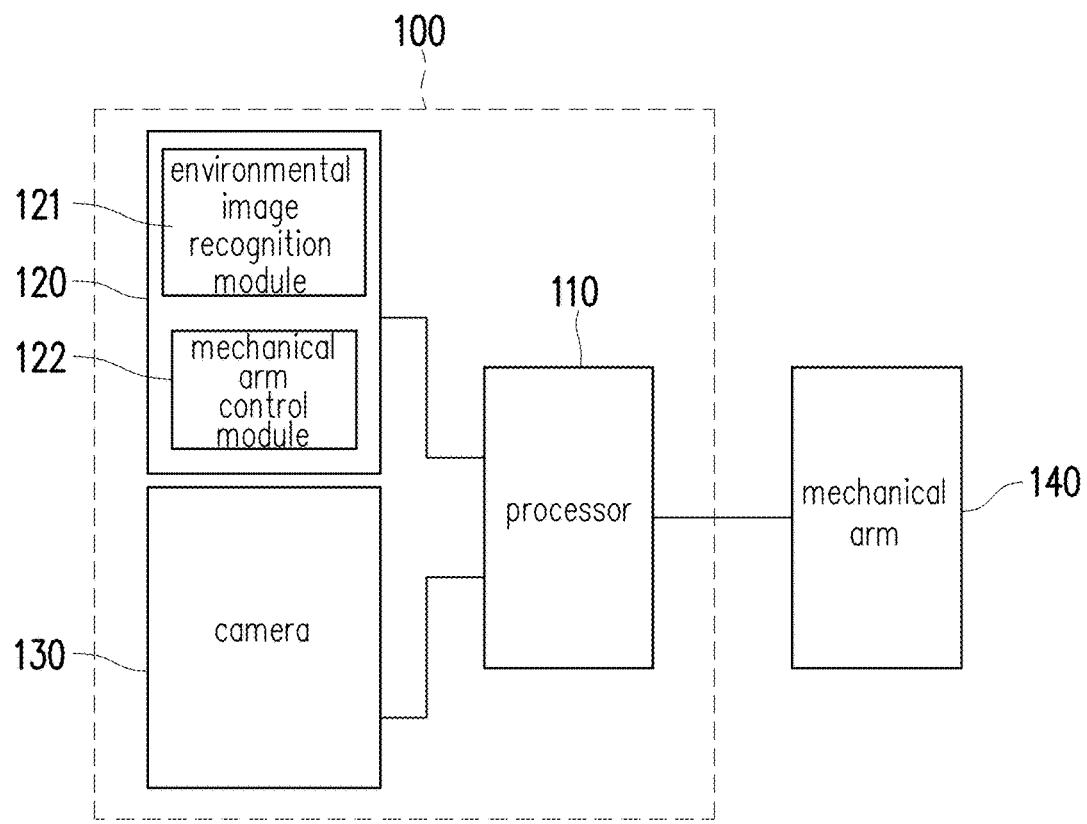
FIG. 1 is a block schematic view of an automatic control system according to an embodiment of the disclosure.

In order to make the disclosure more comprehensible, several embodiments are described below as examples of implementation of the disclosure. Moreover, elements/components/steps with the same reference numerals are used to represent the same or similar parts in the drawings and embodiments.

FIG. 1 is a block schematic view of an automatic control system according to an embodiment of the disclosure. With reference to FIG. 1, an automatic control system 100 includes a processor 110, a memory 120, and a depth camera 130. The processor 110 is coupled to the memory 120, the depth camera 130, and a mechanical arm 140. The mechanical arm 140 may be a multi-axis mechanical arm (e.g., six-axis). In this embodiment, the memory 120 may store an environmental image recognition module 121 and a mechanical arm control module 122. The processor 110 may access the memory 120 and executes the environmental image recognition module 121 and the mechanical arm control module 122 to control the mechanical arm 140 to perform movement and related operations. In this embodiment, the processor 110 and the memory 120 may be integrated into a computer host and may communicate with the depth camera 130 and the mechanical arm 140 through a wired or wireless manner. Nevertheless, in an embodiment, the processor 110 and the memory 120 may also be integrated into a cloud server system, which should however not be construed as limitations to the disclosure.

In this embodiment, the processor 110 may obtain a color image corresponding to a target position and the mechanical arm and depth information corresponding to the color image first through the depth camera 130, executes the environmental image recognition module 121 next according to the color image and the depth information corresponding to the color image, and recognizes an environment of the target position through a computer vision image processing manner. The processor 110 may output a displacement or path parameter corresponding to an environment recognition result according to the environmental image recognition module 121 to execute the mechanical arm control module 122, such that the mechanical arm control module 122 may generate a corresponding control signal to the mechanical arm 140. In this embodiment, the mechanical arm control module 122 may include an input interface (e.g., a socket or API manner and the like) for the mechanical arm 140, and the mechanical arm control module 122 may execute an operation of forward and inverse kinematics of the mechanical arm 140. As such, the mechanical arm control module 122 may control the mechanical arm 140 to automatically move to the target position in a space and to effectively avoid an obstacle in the environment.

In this embodiment, the processor 110 may include a central processing unit (CPU), a programmable microprocessor for general or special use, a digital signal processor (DSP), a programmable controller, an application specific integrated circuit (ASIC), a graphics processing unit (GPU), other similar elements, or a combination of the foregoing elements, and may be configured to implement related functional circuits of the disclosure.

In this embodiment, the memory 120 may include, for example, a random-access memory (RAM), a read-only memory (ROM), an optical disc, a magnetic disk, a hard drive, a solid-state drive, a flash drive, a security digital (SD) card, a memory stick, a compact flash (CF) card, or a storage device of any type. In this embodiment, the memory 120 may be configured to store related modules, related image data, and related parameters provided in the embodiments of the disclosure, so that the processor 110 may execute related data processing and operations through accessing the memory 120.

Figure 2:
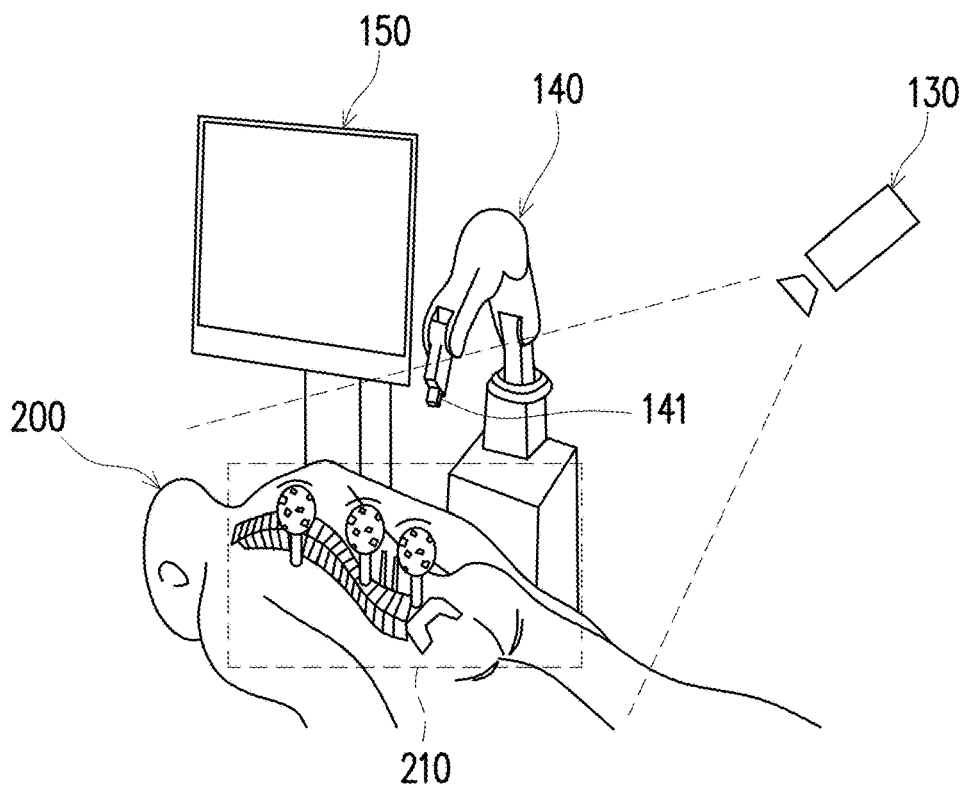
FIG. 2 is a schematic view of operation of the automatic control system according to an embodiment of the disclosure.

FIG. 2 is a schematic view of operation of the automatic control system according to an embodiment of the disclosure. With reference to FIG. 1 and FIG. 2, the automatic control system 100 in FIG. 1 may be applied to, for example, a medical surgery situation as shown in FIG. 2, and the mechanical arm 140 may be a surgical mechanical arm. As shown in FIG. 2, the processor 110 of the automatic control system 100 may further be coupled to a display apparatus 150. To be specific, the depth camera 130 may perform shooting towards a surgical location 210 of a surgical object 200, so as to continuously obtain a plurality of color images corresponding to the surgical location 210 and a plurality of depth information corresponding to the color images. The depth camera 130 may provide the color images and the depth information corresponding to the color images to the processor 110. The processor 110 may correspondingly display related real-time information on the display apparatus 150 according to a shooting result of the depth camera 130 for medical personnel to make judgment or perform monitoring, and display content of the display apparatus 150 is not limited by the disclosure. In this embodiment, the processor 110 may perform image processing on each one of the color images and the corresponding depth information to generate a corresponding control signal to the mechanical arm 140, such that the mechanical arm 140 may automatically face the target position of the surgical location 210.

In a process when the depth camera 130 performs continuous shooting, the processor 110 performs continuous visual image processing as well to continuously output the control signal to the mechanical arm 140. In other words, the processor 110 may correspondingly control movement of the mechanical arm 140 corresponding to a current environmental situation or an environmental change. For instance, the processor 110 may control or operate a clip 141 of the mechanical arm 140 to move towards a specific medical device in the surgical location 210, and when the mechanical arm 140 moves, the mechanical arm 140 may automatically avoid an obstacle (including a body portion of the surgical object 200) in a surgical environment, such that the clip 141 of the mechanical arm 140 may smoothly clip the specific medical device on the target position. Therefore, the automatic control system 100 provided by this embodiment may control the mechanical arm 140 to effectively assist or work with the medical personnel in performing related surgical actions.

Figure 3:
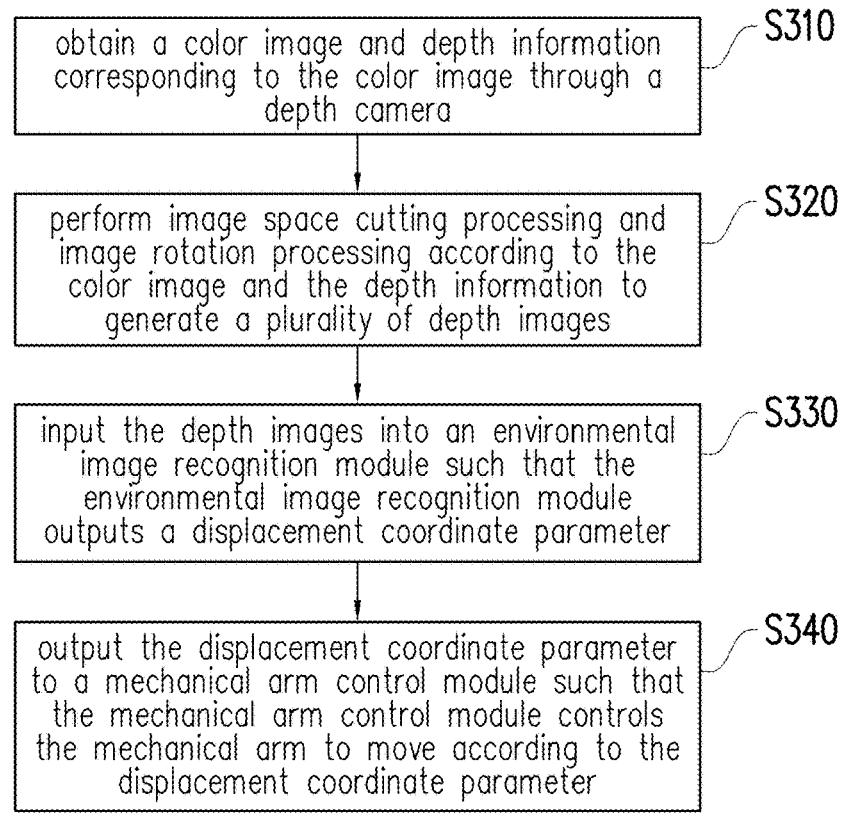
FIG. 3 is a flowchart of an automatic control method according to an embodiment of the invention.

FIG. 3 is a flowchart of an automatic control method according to an embodiment of the disclosure. With reference to FIG. 1 to FIG. 3, the automatic control system 100 may implement control of the mechanical arm 140 to perform automatic movement through performing steps S310 to S340. In step S310, the processor 110 may obtain a color image and depth information corresponding to the color image through the depth camera 130. In step S320, the processor 110 may perform image space cutting processing and image rotation processing according to the color image and the depth information to generate a plurality of depth images. In step S330, the processor 110 may input the depth images into the environmental image recognition module 121, such that the environmental image recognition module 121 outputs a displacement coordinate parameter. In this embodiment, the environmental image recognition module 121 may include a neural network operation module, and the environmental image recognition module 121 may be, for example, pre-trained to learn to recognize obstacles in the depth images and generates the displacement coordinate parameter according to a recognition result of the depth images. In step S340, the environmental image recognition module 121 may output the displacement coordinate parameter to a mechanical arm control module 122 such that the mechanical arm control module 122 controls the mechanical arm 140 to move according to the displacement coordinate parameter. Therefore, the automatic control system 100 of this embodiment may effectively control the mechanical arm 140. Further, specific implementation details of each step are described in detail through the following embodiments.

Figure 4:
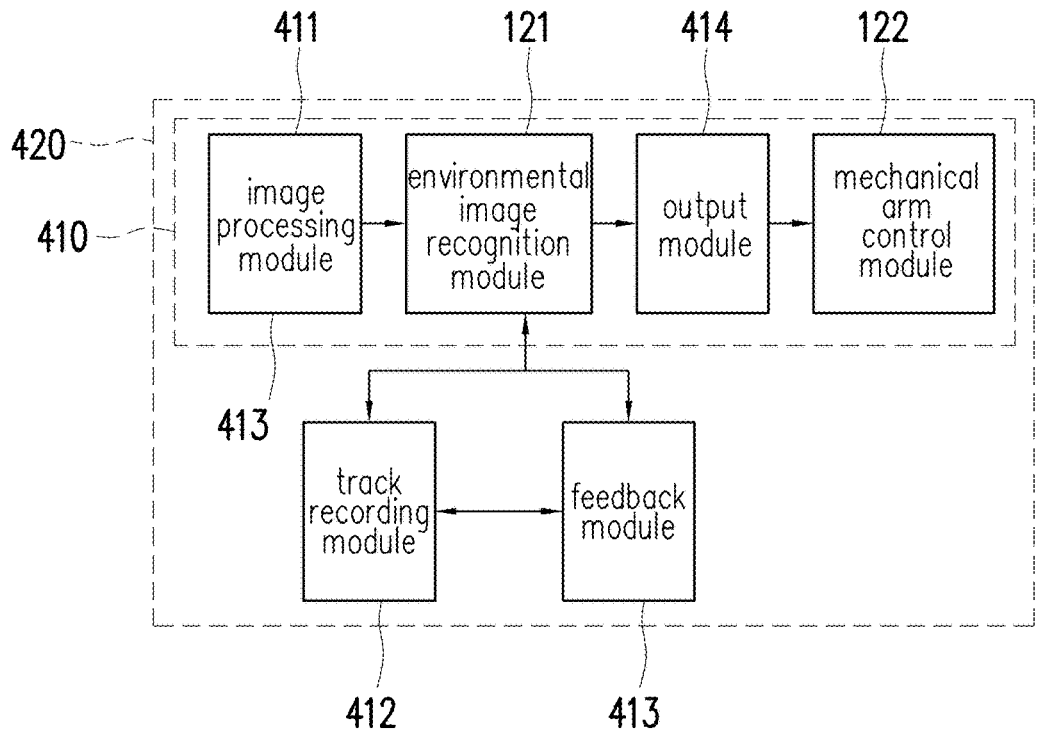
FIG. 4 is a schematic view of a plurality of modules of a neural network operation according to an embodiment of the disclosure.
Figure 5:
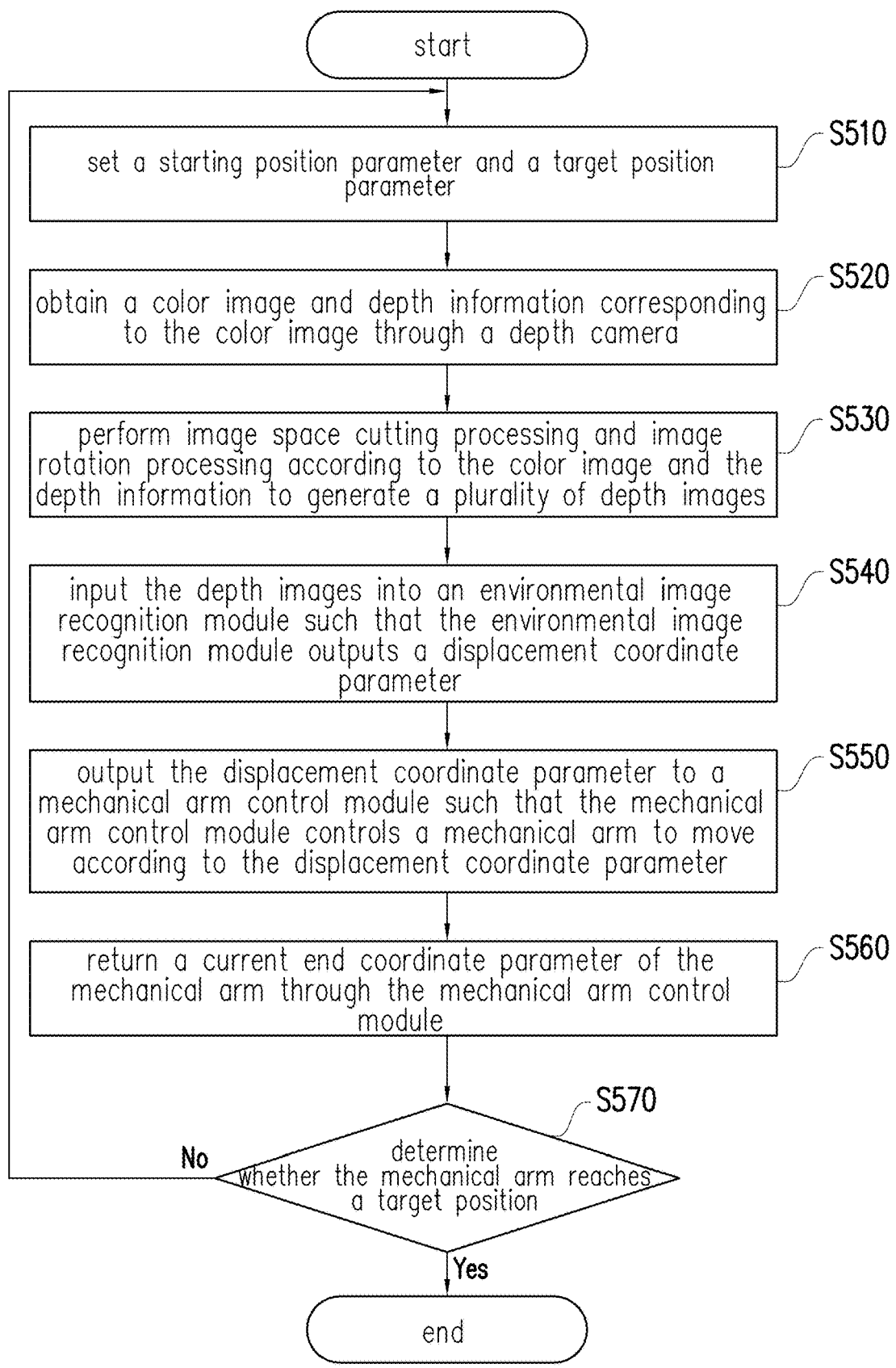
FIG. 5 is a flowchart of an automatic control method according to another embodiment of the disclosure.

FIG. 4 is a schematic view of a plurality of modules of a neural network operation according to an embodiment of the disclosure. FIG. 5 is a flowchart of an automatic control method according to another embodiment of the disclosure. With reference to FIG. 1, FIG. 4, and FIG. 5, the automatic control system 100 may perform steps S510 to S570 to operate the mechanical arm 140. In this embodiment, the memory 120 may further store an image processing module 411, a track recording module 412, a feedback module 413, and an output module 414. The processor 110 may execute the environmental image recognition module 121 and the mechanical arm control module 122, the image processing module 411, the track recording module 412, the feedback module 413, and the output module 414. Note that the automatic control system 100 may execute the image processing module 411, the environmental image recognition module 121, the output module 414, and the mechanical arm control module 122 to control the mechanical arm 140. The image processing module 411, the environmental image recognition module 121, the output module 414, and the mechanical arm control module 122 may belong to or may be integrated as a control module 410. Further, in an embodiment, the automatic control system 100 may enter a training mode to train the environmental image recognition module 121. Accordingly, the automatic control system 100 may execute the image processing module 411, the environmental image recognition module 121, the track recording module 412, the feedback module 413, the output module 414, and the mechanical arm control module 122 to train the environmental image recognition module 121. The image processing module 411, the environmental image recognition module 121, the track recording module 412, the feedback module 413, the output module 414, and the mechanical arm control module 122 may belong to or may be integrated as a training module 420.

Figure 6:
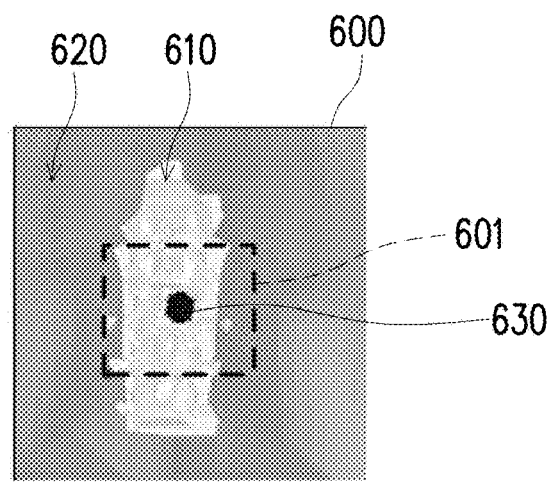
FIG. 6 is a schematic view of a color image according to an embodiment of the disclosure.
Figure 7:
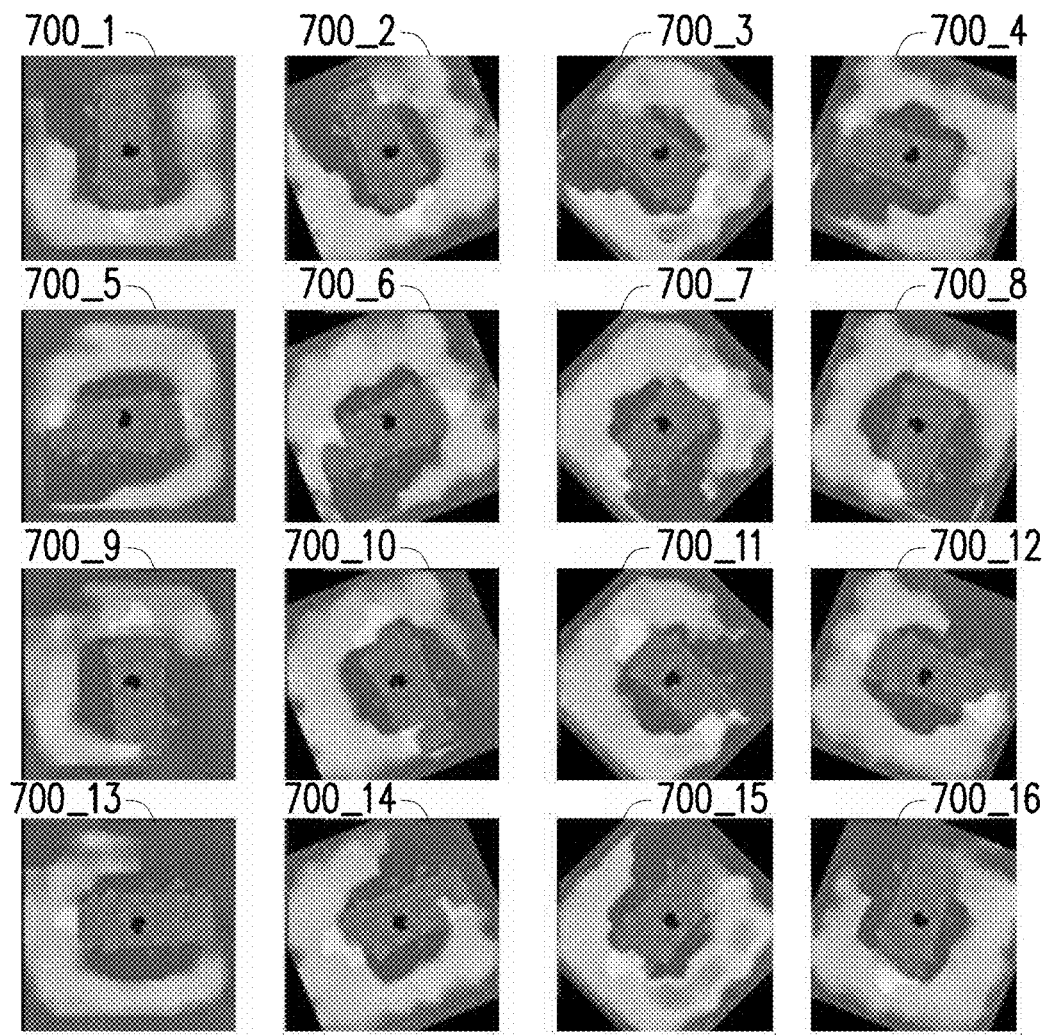
FIG. 7 is a schematic view of a plurality of depth images according to an embodiment of the disclosure.

FIG. 6 is a schematic view of a color image according to an embodiment of the disclosure. FIG. 7 is a schematic view of a plurality of depth images according to an embodiment of the disclosure. Accordingly, description is provided as follows together with FIG. 6 and FIG. 7. In this embodiment, the automatic control system 100 may further include an input module, such as input equipment including a mouse, a keyboard, etc. and may receive input data (or a setting parameter) of a user. In step S510, the processor 110 may set a starting position parameter and a target position parameter according to the received input data. In step S520, the processor 110 may obtain a color image 600 of a current frame as shown in FIG. 6 and depth information corresponding to the color image 600 through the depth camera 130. The color image 600 may include a surgical site image 610 and an environmental image 620. The processor 110 may define a target position 630 in the color image 600 according to the target position parameter and a range 601 of the target position 630. In step S530, the processor 110 may execute the image processing module 411 and perform image space cutting processing and image rotation processing according to the color image 600 and the depth information to generate a plurality of depth images 700_1 to 700_16 as shown in FIG. 7.

For instance, the image processing module 411 may perform RGB digital image space cutting first on the color image 600 to enhance environmental characteristic difference, so that the depth images 700_1, 700_5, 700_9, and 700_13 corresponding to different depths are generated. Next, the image processing module 411 may rotate the depth images 700_1, 700_5, 700_9, and 700_13 by, for example, 90 degrees, 180 degrees, and 270 degrees, so as to further generate a plurality of depth images 700_2 to 700_4, 700_6 to 700_8, 700_10 to 700_12, 700_14 to 700_16 and to increase sample data. From another perspective, 16 pieces of sample data are provided on every pixel position in each image. In other words, the automatic control system 100 may process one color image obtained by the depth camera 130 in each frame to generate the plurality of corresponding depth images 700_1 to 700_16, so as to effectively analyze an environmental state of a current space at each moment in a three-dimensional manner. Besides, the number of the depth images provided by the disclosure is not limited to FIG. 7.

In step S540, the processor 110 may input the depth images into the environmental image recognition module 121, such that the environmental image recognition module 121 outputs the displacement coordinate parameter to the output module 414. In this embodiment, the environmental image recognition module 121 may execute the neural network operation, and the environmental image recognition module 121 may recognize an effective safe space image from the depth images 700_1 to 700_16, so as to select one of the depth images 700_1 to 700_16 as the effective safe space image and further determine the displacement coordinate parameter according to the effective safe space image. In other words, the environmental image recognition module 121 may determine a safe moving path in the space of the current frame in a three-dimensional manner, so as to provide the corresponding displacement coordinate parameter to the output module 414.

To be more specific, after each of the depth images 700_1 to 700_16 is inputted to the a neural network operation model of the environmental image recognition module 121, the neural network operation model of the environmental image recognition module 121 may perform eigenvalue (environmental effective space eigenvalue) analysis on a plurality of pixels of each of the depth images 700_1 to 700_16, so as to obtain a eigenvalue weight of each pixel, where the eigenvalue analysis is configured to determine object evaluation of each pixel. Therefore, the environmental image recognition module 121 may generate, for example, a plurality of spatial weight matrix data corresponding to the depth images 700_1 to 700_16. Accordingly, the environmental image recognition module 121 may perform the neural network operation according to the spatial weight matrix data corresponding to the depth images 700_1 to 700_16 to determine the effective safe space image.

For instance, the neural network operation model of the environmental image recognition module 121 may determine a safe displacement direction and position of a next frame according to a current position of the mechanical arm 140 in each one of the depth images 700_1 to 700_16. For instance, a weight belonging to an object (the obstacle or the surgical site) may be high in the depth images 700_1 to 700_16. The environmental image recognition module 121 may determine a minimum weight value corresponding to each pixel within a surrounding unit moving distance of each current position of the mechanical arm 140 in each of the depth images 700_1 to 700_16 (and moves towards the target position) as the position of the mechanical arm 140 in the next frame and treats the corresponding depth image as the effective safe space image. Therefore, the automatic control system 100 may drive the mechanical arm 140 to move towards this position, so that the mechanical arm 140 is effectively prevented from contacting or colliding with the object (the obstacle or the surgical site).

In step S550, the output module 414 may output the displacement coordinate parameter to the mechanical arm control module 122 such that the mechanical arm control module 122 controls the mechanical arm 140 to move according to the displacement coordinate parameter. In this embodiment, the output module 414 may further output movable direction information and movable position information for the mechanical arm 140 to the mechanical arm control module 122 according to analysis and operation results of the environmental image recognition module 121. In step S560, the processor 110 may return a current end coordinate parameter (e.g., coordinates of the clip 141 of the mechanical arm 140 as shown in FIG. 2) of the mechanical arm 140 through the mechanical arm control module 122. In step S570, the processor 110 may determine whether the mechanical arm 140 reaches the target position. If yes, the automatic control system 100 ends a current control task. If no, the automatic control system 100 performs steps S510 to S570 again to determine a next displacement direction and position of the mechanical arm 140 based on a color image and depth information thereof the next frame provided by the depth camera 130. Therefore, in the automatic control system 100 and the automatic control method provided by this embodiment, movement of the mechanical arm 140 in the space may be effectively controlled through a visual image control manner, so that the mechanical arm 140 is prevented from contacting or colliding with the object (the obstacle or the surgical site) when moving in the space.

Figure 8:
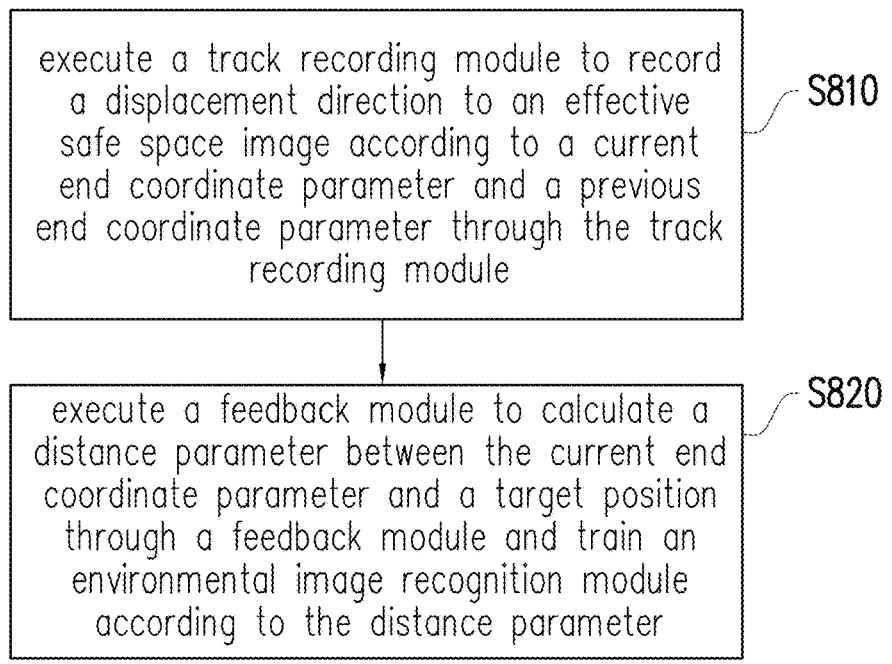
FIG. 8 is a flowchart of training of a neural network operation module according to an embodiment of the disclosure.
Figure 9:
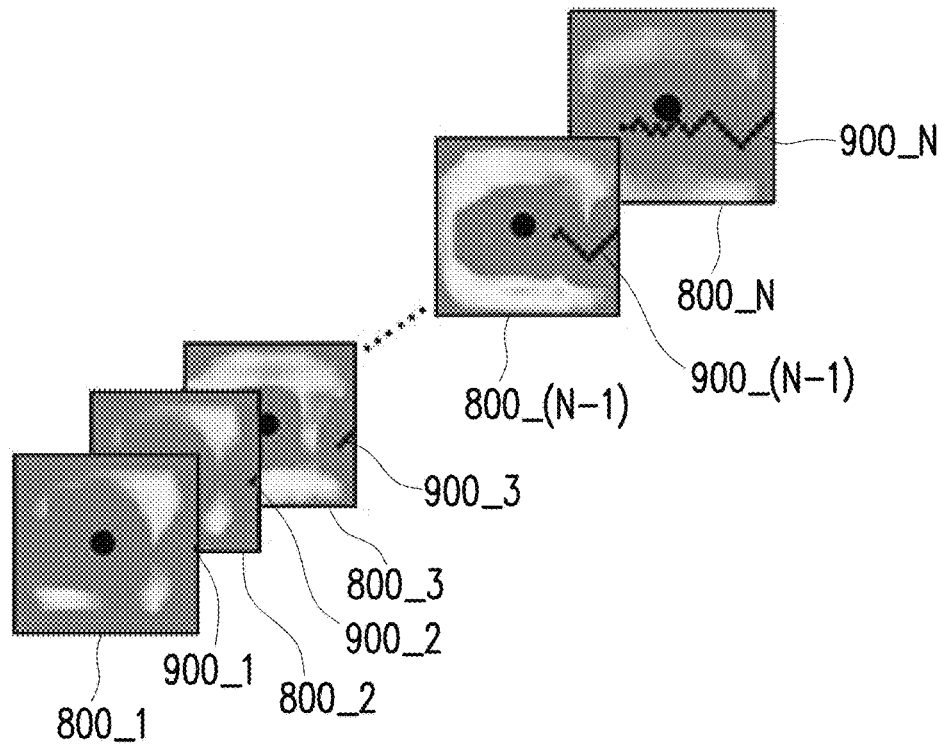
FIG. 9 is a schematic view of a plurality of effective safe space images according to an embodiment of the disclosure.

FIG. 8 is a flowchart of training of an environmental image recognition module according to an embodiment of the disclosure. FIG. 9 is a schematic view of a plurality of effective safe space images according to an embodiment of the disclosure. With reference to FIG. 1, FIG. 4, FIG. 5, FIG. 8, and FIG. 9, the automatic control system 100 may execute steps S510 to S570, S810, and S820 to train the neural network operation model in the environmental image recognition module 121. The automatic control system 100 may enter the training mode to execute the training module 420. In this embodiment, the automatic control system 100 may performs steps S510 to S570 in sequence according to the flowchart provided by the embodiment of FIG. 5, and after the processor 110 returns the current end coordinate parameter of the mechanical arm 140 through the mechanical arm control module 122 (after step S560), the automatic control system 100 may perform step S810. In step S810, the processor 110 may execute the track recording module 412 to record a displacement direction to an effective safe space image 800_1 as shown in FIG. 9 according to the current end coordinate parameter and a previous end coordinate parameter through the track recording module 412, where the effective safe space image 800_1 includes a moving tack 900_1 of the mechanical arm 140.

Next, in step S820, the processor 110 may execute the feedback module 413 to calculate a distance parameter between the current end coordinate parameter and the target position through the feedback module 413 and trains the environmental image recognition module 121 according to the distance parameter. For instance, the processor 110 may determine whether a result of current movement of the mechanical arm 140 makes the mechanical arm 140 move towards the target position (whether a distance between the mechanical arm 140 and the target position decreases), so as to define whether the current movement is appropriate to further feedback and train the neural network operation model in the environmental image recognition module 121. Finally, the processor 110 may continue to perform step S570. Further, the automatic control system 100 may, for example, repeatedly analyze shooting results of a plurality of frames of the depth camera 130 for a continuous period of time to generate a plurality of continuous effective safe space images 800_1 to 800_N as shown in FIG. 9, where N is a positive integer greater than 1. Note that the effective safe space images 800_1 to 800_N may include movement tracks 900_1 to 900_N formed by a plurality of displacement positions of the mechanical arm 140 in a plurality of previous frames accumulated and recorded in a time sequence. In other words, the neural network operation model in the environmental image recognition module 121 may effectively recognize the object in the image, the automatic control system 100 may further effectively train the result outputted by the neural network operation model to drive the mechanical arm 140 to move towards the target position and select an optimal path, such that each movement made by the mechanical arm 140 is not simply performed to avoid the obstacle in the environment.

In view of the foregoing, in the automatic control method of the mechanical arm and the automatic control system provided by the disclosure, the neural network operation model in the environmental image recognition module may learn to determine the object in the image and learn the displacement coordinate parameter of each neural network operation result through visual training, such that the mechanical arm may move towards the target position. Therefore, in the automatic control method and the automatic control system provided by the disclosure, the mechanical arm may be effectively controlled to move towards the target position, and the mechanical arm may effectively avoid the obstacle in the environment when moving.

In order to make the invention more comprehensible, several embodiments are described below as examples of implementation of the invention. Moreover, elements/components/steps with the same reference numerals are used to represent the same or similar parts in the drawings and embodiments.

What is claimed is:

1. An automatic control method of a mechanical arm, comprising:
    obtaining a color image and depth information corresponding to the color image through a depth camera;
    performing image space cutting processing and image rotation processing according to the color image and the depth information to generate a plurality of depth images;
    inputting the depth images into a neural network operation model of a processor for outputting a displacement coordinate parameter, comprising:
        performing eigenvalue analysis on each of the depth images to generate spatial weight matrix data corresponding to the depth images; and
        determining a minimum weight value of the spatial weight matrix data as a position of the mechanical arm in a next frame, and treating the one corresponding depth image as an effective safe space image; and
    outputting the displacement coordinate parameter such that the processor controls the mechanical arm to move toward the position with the minimum weight value according to the displacement coordinate parameter.

2. The automatic control method according to claim 1, further comprising:
    setting a starting position parameter and a target position parameter, wherein the starting position parameter corresponds to an end position parameter of the mechanical arm.

3. The automatic control method according to claim 2, wherein the image space cutting processing and the image rotation processing are performed according the target position parameter or a position parameter of an obstacle.

4. The automatic control method according to claim 2, wherein the processor is configured to execute a neural network operation, and the processor is configured to recognize the effective safe space image from the depth images and determines the displacement coordinate parameter according to the effective safe space image.

5. The automatic control method according to claim 4, further comprising:
    returning a current end coordinate parameter of the mechanical arm through the processor after the mechanical arm moves according to the displacement coordinate parameter.

6. The automatic control method according to claim 5, wherein the step of inputting the depth images into the neural network operation model further comprises:

recording a displacement direction to the effective safe space image according to the current end coordinate parameter and a previous end coordinate parameter; and calculating a distance parameter between the current end coordinate parameter and a target position and training the neural network operation model according to the distance parameter.

7. The automatic control method according to claim 4, wherein the step of inputting the depth images into the neural network operation model comprises:

analyzing the depth images through the neural network operation model to generate the spatial weight matrix data corresponding to the depth images; and performing the neural network operation according to the spatial weight matrix data corresponding to the depth images through the neural network operation model to determine the effective safe space image.

8. The automatic control method according to claim 7, wherein the step of outputting the displacement coordinate parameter comprises:

further outputting movable direction information and movable position information for the mechanical arm according to analysis and operation results of the neural network operation model.

9. An automatic control system of a mechanical arm, comprising:

a depth camera, configured to obtain a color image and depth information corresponding to the color image; and a processor, coupled to the mechanical arm and the depth camera, configured to perform image space cutting processing and image rotation processing according to the color image and the depth information to generate a plurality of depth images, wherein the processor inputs the depth images into a neural network operation model of the processor for outputting a displacement coordinate parameter, wherein the processor performs eigenvalue analysis on each of the depth images to generate spatial weight matrix data corresponding to the depth images, the processor determines a minimum weight value of the spatial weight matrix data as a position of the mechanical arm in a next frame, and the processor treats the one corresponding depth image as an effective safe space image; and the processor outputs the displacement coordinate parameter such that the processor controls the mechanical arm to move toward the position with the minimum weight value according to the displacement coordinate parameter.

10. The automatic control system according to claim 9, wherein the processor sets a starting position parameter and a target position parameter, wherein the starting position parameter corresponds to an end position parameter of the mechanical arm.

11. The automatic control system according to claim 10, wherein the processor executes the image space cutting processing and the image rotation processing according to the target position parameter and a position parameter of an obstacle.

12. The automatic control system according to claim 10, wherein the processor is configured to execute a neural network operation, and the processor is configured to recognize the effective safe space image from the depth images and to determine the displacement coordinate parameter according to the effective safe space image.

13. The automatic control system according to claim 12, wherein the processor returns a current end coordinate parameter of the mechanical arm after the mechanical arm moves according to the displacement coordinate parameter.

14. The automatic control system according to claim 13, wherein the processor records a displacement direction to the effective safe space image according to the current end coordinate parameter and a previous end coordinate parameter, and the processor calculates a distance parameter between the current end coordinate parameter and a target position and trains the neural network operation model according to the distance parameter.

15. The automatic control system according to claim 12, wherein the processor analyzes the depth images through the neural network operation model to generate the spatial weight matrix data corresponding to the depth images, and the processor performs the neural network operation according to the spatial weight matrix data corresponding to the depth images through the neural network operation model to determine the effective safe space image.

16. The automatic control system according to claim 15, wherein the processor further outputs movable direction information and movable position information for the mechanical arm to the mechanical arm control module according to analysis and operation results of the neural network operation model.

* * * * *